United States Patent [19]
Gerner et al.

[11] Patent Number: 6,152,177
[45] Date of Patent: Nov. 28, 2000

[54] METHOD AND APPARATUS FOR AUTO-ZEROING A FLOW SENSOR

[75] Inventors: Yuri Gerner, Mendota Heights; Carl W. Sims, St. Paul; Benjamin L. Behler, Maplewood; Kurt P. Hamberg, Fridley, all of Minn.

[73] Assignee: Systec Inc., New Brighton, Minn.

[21] Appl. No.: 09/417,869

[22] Filed: Oct. 13, 1999

[51] Int. Cl.[7] ..................................................... F16K 11/85
[52] U.S. Cl. ........................................ 137/625.29; 73/134
[58] Field of Search ......................... 137/625.29; 73/1.16, 73/1.34

[56] References Cited

U.S. PATENT DOCUMENTS

| | | |
|---|---|---|
| 3,521,673 | 7/1970 | Gruner et al. ..................... 137/625.29 |
| 4,253,156 | 2/1981 | Lisle et al. . |
| 4,419,880 | 12/1983 | Hanowich . |
| 4,716,923 | 1/1988 | West .................................. 137/625.29 |
| 4,948,389 | 8/1990 | Klein et al. . |
| 4,961,348 | 10/1990 | Bonne . |
| 5,524,084 | 6/1996 | Wang et al. . |
| 5,542,286 | 8/1996 | Wang et al. . |
| 5,548,990 | 8/1996 | Northedge . |
| 5,576,487 | 11/1996 | Gimson . |
| 5,684,246 | 11/1997 | Korpi . |

*Primary Examiner*—John Fox
*Attorney, Agent, or Firm*—Haugen Law Firm PLLP

[57] ABSTRACT

In a gas chromatograph a valve assembly for providing gradual, uninterrupted re-direction of gas flow between a flow measurement position and a bypass position. The valve assembly maintains constant gas flow through the chromatograph during transition between an auto-zeroing mode in which a flow sensor is calibrated and a flow measurement mode. The valve assembly includes a valve rotor having eccentric grooves formed for providing the desired re-direction of gas flow.

8 Claims, 4 Drawing Sheets

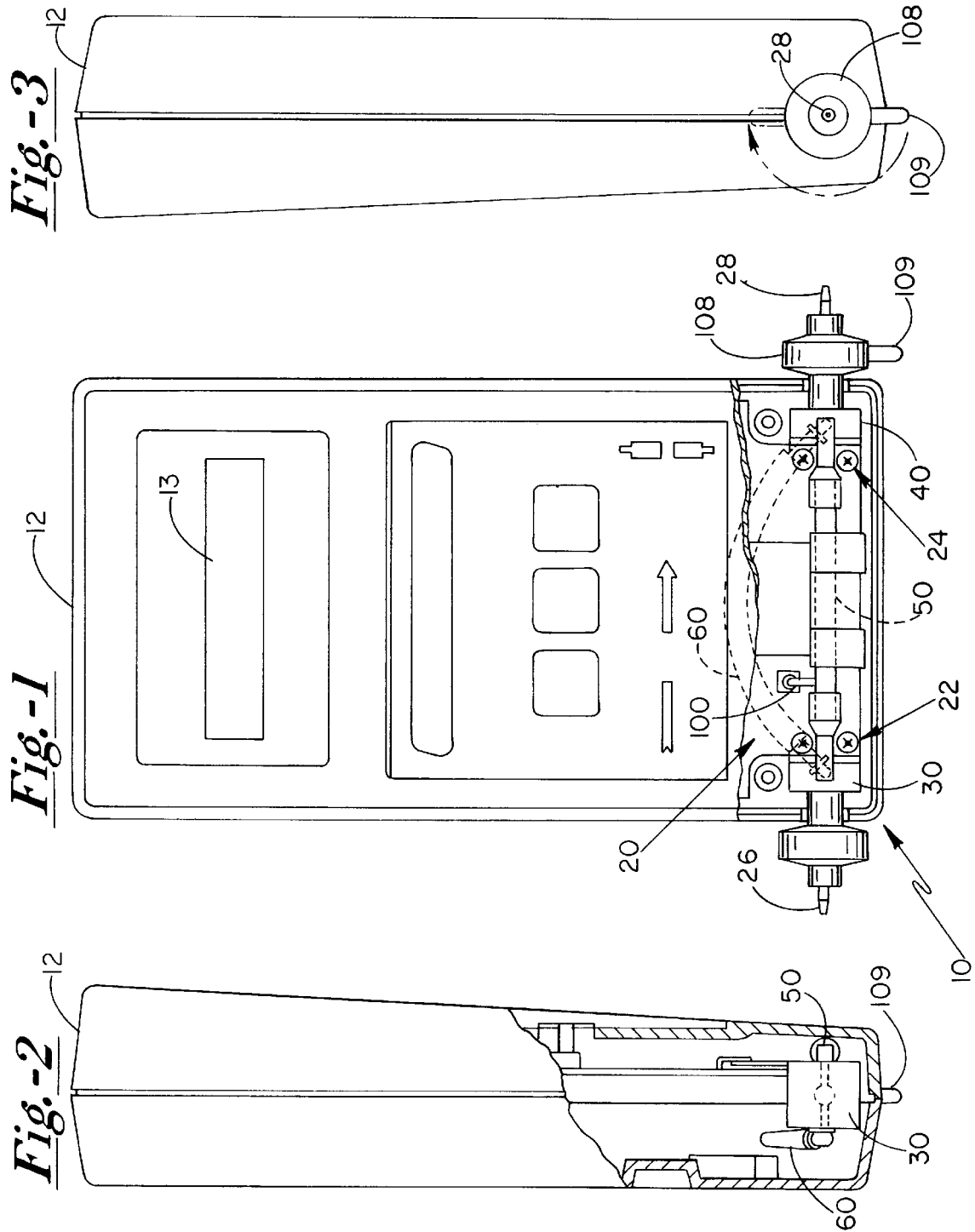

METHOD AND APPARATUS FOR AUTO-ZEROING A FLOW SENSOR

BACKGROUND OF THE INVENTION

I. Field of the Invention

The present invention relates to a method and apparatus for auto-zeroing a flow sensor in a gas chromatograph while maintaining constant gas flow through the chromatograph and more particularly pertains to a two position, three-way integrated valve assembly for providing gradual, uninterrupted re-direction of gas flow from a flow measurement position to a bypass position wherein auto-zeroing of the flow sensor is accomplished.

II. Description of the Prior Art

In the practice of gas chromatography, accurate knowledge of the flow rate of the mobile phase is of critical importance. It is known in the art to measure the flow rate by means of flow sensors which are calibrated for specific carrier gasses. This calibration generally provides for a zero flow measurement. However, flow sensor output is subject to short term drift, which is largely temperature dependent, and long term drift, which is related to sensor fabrication techniques.

Methods and apparatus for correcting for sensor output drift are known in the prior art. One such method is disclosed in U.S. Pat. No. 5,542,286 to Wang et al. The input valves controlling the input into the chromatograph are shut, reducing the internal flow to zero. The indicated rate of flow is then measured using the flow sensor. If the value measured by the flow sensor during this test is different than the originally calibrated offset by some predetermined amount, then the newly measured value replaces the stored offset value. In a chromatograph where some minimum internal gas or liquid flow is necessary to prevent contamination of the instrument, a three-way valve can direct liquid or gas flow away from the flow sensor during the calibration run without eliminating internal flow through the chromatograph. The Wang et al. apparatus does not however provide for gradual, uninterrupted re-direction of gas flow from a flow measurement position to a bypass position and therefore suffers from pressure hammering which is a potential source of damage to the flow sensor or other components in the flow path.

It would therefore be desirable to provide a method and apparatus for auto-zeroing a flow sensor in a gas chromatograph which overcomes this deficiency in the prior art.

SUMMARY OF THE INVENTION

Accordingly, it is a primary object of the present invention to provide a method and apparatus for auto-zeroing a flow sensor in a gas chromatograph which provides for the gradual, uninterrupted re-direction of gas flow between the flow measurement position and the bypass position.

It is a further object of the applicant's invention to provide a two position, three-way valve assembly including a valve rotor having a pair of eccentric grooves formed proximate opposite ends of the rotor, the eccentric grooves being operable to provide the gradual, uninterrupted re-direction of gas flow between the flow measurement position and the bypass position.

It is another object of the invention to provide a valve assembly which maintains constant gas flow through the chromatograph.

It is yet another object of the invention to provide a switch means operably coupled to the valve rotor for initiating an auto-zeroing routine in a microprocessor when the valve assembly is in the bypass position.

Various of the foregoing objects, advantages and distinctions of the invention are particularly obtained in a valve assembly having an inlet valve and an outlet valve disposed in spaced relationship one to the other inside a housing. A flow sensor line and a bypass line are disposed between the inlet valve and outlet valve, each of the flow sensor line and bypass line being in fluid communication with the inlet valve and the outlet valve, the flow sensor line through a flow sensor passageway formed in an inlet valve body and a flow sensor passageway formed in an outlet valve body and the bypass line through a bypass passageway formed in the inlet valve body and a bypass passageway formed in the outlet valve body. A valve rotor comprising a cylindrical rod extends between the inlet valve and the outlet valve. A valve rotor inlet end is receivable in the inlet valve body and an outlet end is receivable in the outlet valve body. The valve rotor further includes an inlet passageway formed at the inlet end for communication with a fluid source and alternate fluid communication with the inlet flow sensor passageway and the inlet bypass passageway. The valve rotor also includes an outlet passageway formed at the outlet end for communication with a gas chromatograph and alternate fluid communication with the outlet flow sensor passageway and the outlet bypass passageway. The inlet passageway further includes a longitudinal portion and a transverse portion aligned with the inlet flow sensor passageway and the inlet bypass passageway, the transverse portion terminating in an eccentric groove formed at a lateral surface of the valve rotor. The outlet passageway similarly further includes a longitudinal portion and a transverse portion aligned with the outlet flow sensor passageway and the outlet bypass passageway, the transverse portion terminating in an eccentric groove formed at the lateral surface of the valve rotor. Rotation of the valve rotor alternately aligns the inlet and outlet transverse portions with the inlet and outlet flow sensor passageway and the inlet and outlet bypass passageways respectively, the eccentric grooves being sized and configured for providing gradual, uninterrupted re-direction of the gas flow while maintaining constant flow therethrough.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a plan view of a flow meter housing partially cut away to show valve assembly of the present invention.

FIG. 2 is a left side elevation view of the housing partially cut away to show the configuration of the flow sensor and bypass lines.

FIG. 3 is a right side elevation view of the housing.

DESCRIPTION OF THE PREFERRED EMBODIMENT

Figure 4:
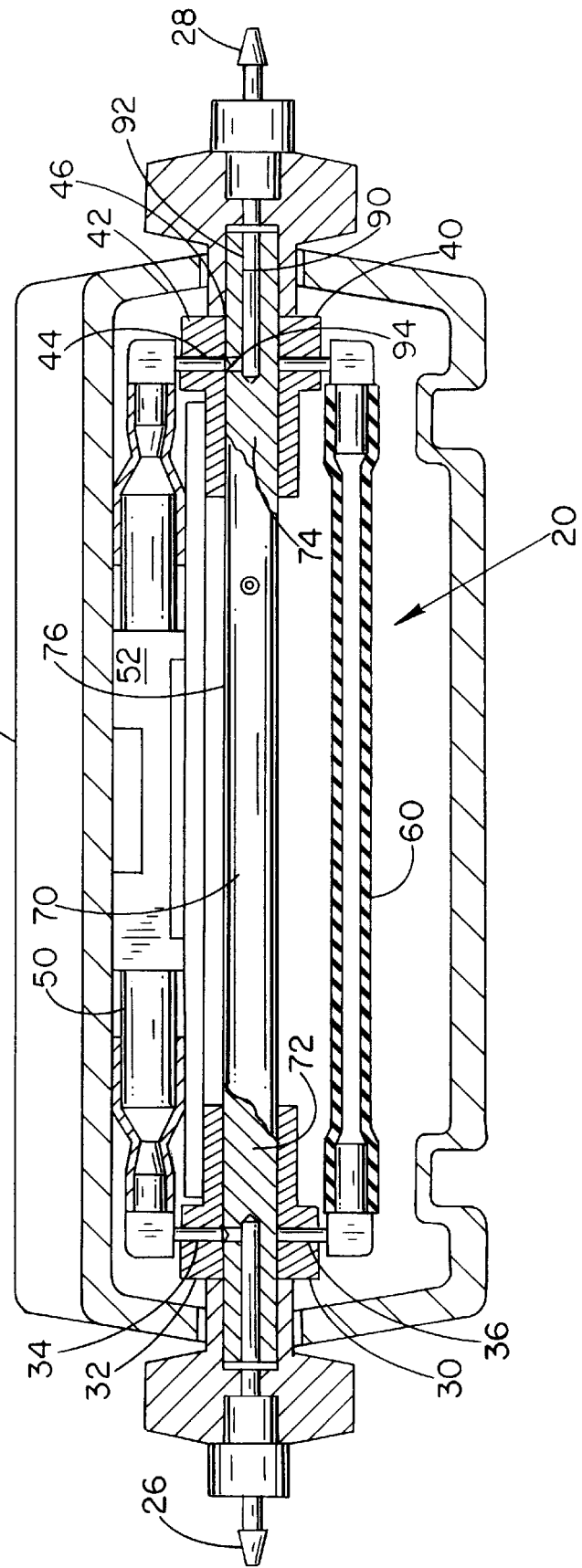
FIG. 4 is a cross sectional view of the valve assembly.

With reference now to the drawings, and in particular to FIG. 1, a flow sensor 10 according to the present invention for use with a gas chromatograph (not shown) is shown including a housing 12 having disposed therein a valve assembly generally designated 20. Valve assembly 20 is operably connectable to a source of gas at an inlet end generally designated 22 and a gas chromatograph at an outlet end generally designated 24 by conventional means such as fittings 26 and 28.

Valve assembly 20 includes an inlet valve 30 and an outlet valve 40 disposed in spaced relationship one to the other (FIG. 4). A flow sensor line 50 and a bypass line 60 are disposed between inlet valve 30 and outlet valve 40 and in fluid communication therewith. The flow sensor line 50 includes means for measuring fluid flow therethrough such as flow sensor 52.

Inlet valve 30 (FIG. 2) further comprises an inlet valve body 32 (FIG. 5) having a flow sensor passageway 34 extending from an inlet valve body inner wall 36 at one end thereof and terminating in communication with the flow sensor line 50. Inlet valve body 32 further includes a bypass passageway 37 formed generally opposite to and aligned with the flow sensor passageway 34 and extending from the inlet valve body inner wall 36 and terminating in communication with the bypass line 60.

Outlet valve 40 has a similar configuration and includes an outlet valve body 42 (FIG. 4) having a flow sensor passageway 44 extending from an outlet valve body inner wall 46 at one end thereof and terminating in communication with the flow sensor line 50. Outlet valve body 42 further includes a bypass passageway 46 formed generally opposite to and aligned with the flow sensor passageway 44 and extending from the outlet valve body inner wall 46 and terminating in communication with the bypass line 60.

A valve rotor 70 includes a cylindrical rod which extends between the inlet valve 30 and the outlet valve 40. An inlet end 72 of the valve rotor 70 is closely received in the inlet valve body 32. An outlet end 74 of the valve rotor 70 is closely received in the outlet valve body 42.

Figure 5:
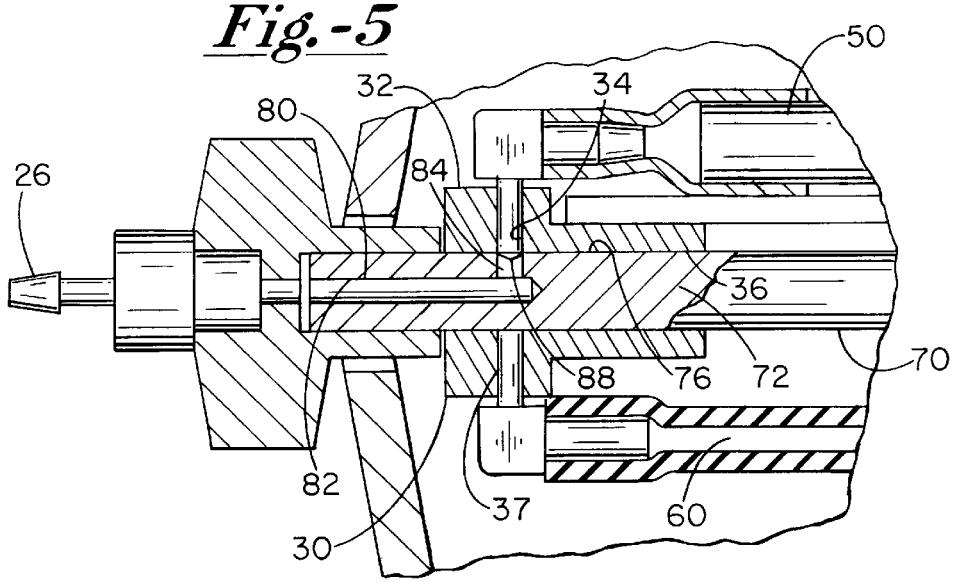
FIG. 5 is a partial cross sectional view showing the inlet valve.

With reference to FIG. 5, the inlet end 72 further includes an inlet passageway 80 having a longitudinal portion 82 and a transverse portion 84. The longitudinal portion 82 is in communication with the fitting 26 at one end thereof and with the transverse portion 84 proximate the other end. The transverse portion 84 is aligned with the inlet flow sensor passageway 34 and the inlet bypass passageway 37 and includes an eccentric groove 88 formed proximate a lateral surface 76 of the valve rotor 70.

Figure 6:
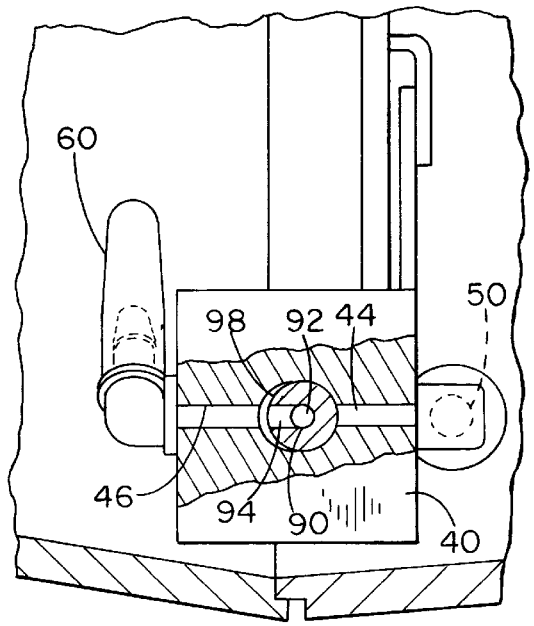
FIG. 6 is a partial cross sectional view showing the eccentric groove.

In similar fashion, the outlet end 72 further includes an outlet passageway 90 having a longitudinal portion 92 and a transverse portion 94 (FIG. 6). The longitudinal portion 92 is in communication with the fitting 28 at one end thereof and with the transverse portion 94 proximate the other end. The transverse portion 94 is aligned with the outlet flow sensor passageway 44 and the outlet bypass passageway 46 and includes an eccentric groove 98 formed proximate a lateral surface 76 of the valve rotor 70.

The transverse portions 84 and 94 are aligned in the valve rotor 70 in such manner that rotation of the valve rotor 70 alternately brings the transverse portions 84 and 94 into communication with the inlet flow sensor passageway 34 and outlet flow sensor passageway 44 in a flow sensor position and into communication with the inlet bypass passageway 37 and outlet bypass passageway 46 in a bypass position. Further, the eccentric grooves 88 and 98 are formed in such manner that rotation of the valve rotor 70 provides for gradual, uninterrupted re-direction of flow through the valve assembly 20 while maintaining constant flow therethrough.

Figure 7:
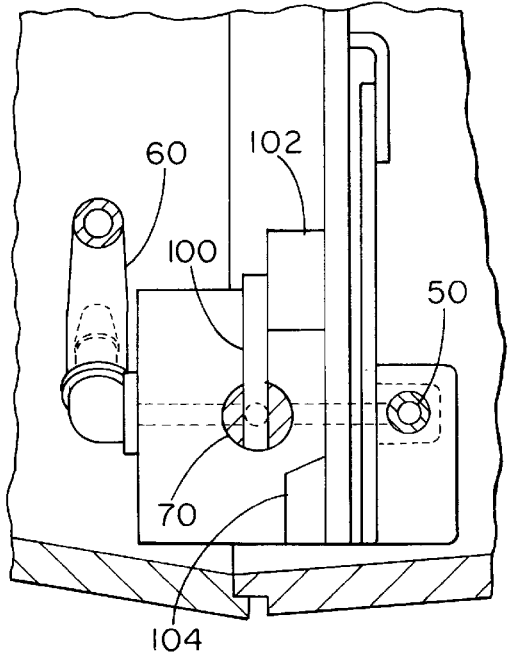
FIG. 7 is a partial cross sectional view showing the switch actuator.

With reference to FIGS. 1 and 7, a switch actuator 100 is shown press fit into valve rotor 70. In the position shown in FIG. 7, the actuator 100 is operable to engage a switch 102 which initiates the auto-zeroing routine of the present invention. In the shown position, gas flow is diverted through the bypass line 60 so that the flow sensor 52 can be calibrated. Rotation of the valve rotor 70 about its axis disengages the actuator 100 from the switch 102 as flow is redirected through the flow sensor line 50. A stop 104 disposed opposite the switch 102 limits the motion of the valve rotor 70 to 180 degrees for easy indication of the position of the valve rotor 70. As shown in FIG. 3, a knob 108 having an indicator 109 is affixed to the valve rotor 70. The indicator 109 provides a reference for the position of the valve rotor 70 and consequently, whether the flow sensor 10 is in an auto-zero mode in which gas flow is diverted from the flow sensor line 50 through the bypass line 60 or in a flow sensing mode in which gas flows through the flow sensor 52.

Figure 8:
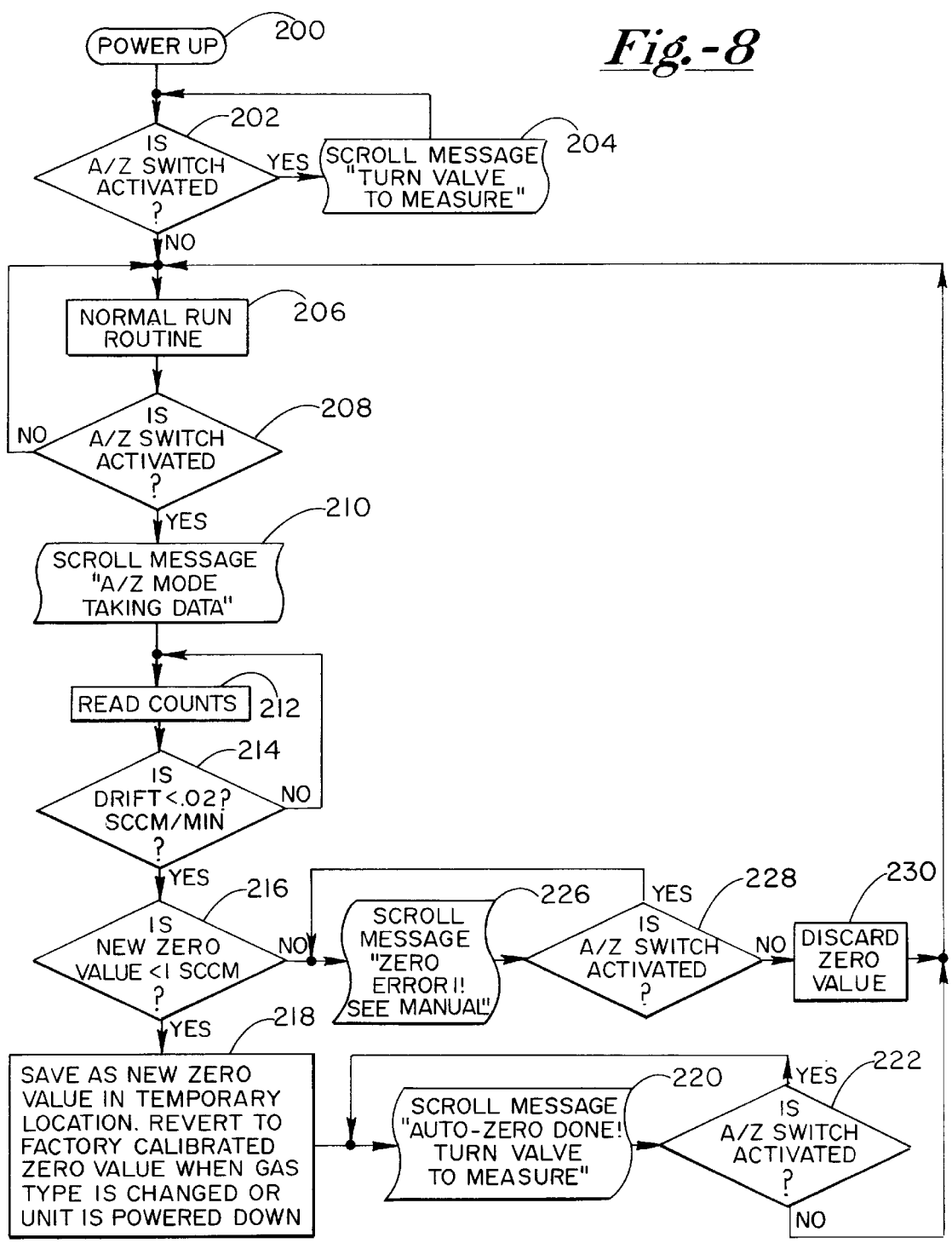
FIG. 8 is a flow diagram of the auto-zeroing routine of the present invention.

A flow diagram showing the operation of the auto-zeroing routine resident in an onboard microprocessor is shown in FIG. 8. After the flow sensor 10 is powered up (200), the condition of switch 102 is checked (202). If the switch 102 is activated, the message "Turn Valve To Measure" is displayed upon display 13 (204) (FIG. 1). If the switch 102 is not activated, the flow sensor 10 performs its normal run routine (206) during which time the condition of switch 102 is periodically polled (208). If the switch 102 is activated (210), the message "A/Z Mode Taking Data" is displayed upon display 13. The count of flow sensor 52 is read (212) and if the drift is not less than 0.02 sccm/min, the system continues reading the count (212) until the drift is less than 0.02 sccm/min. If the new zero value is less than 1 sccm (216), this value is saved in a temporary location and used as the new zero value. The message "Auto-Zero Done! Turn Valve to Measure" is displayed (220) to prompt a user to rotate the knob 108 to initiate the flow sensing mode. This message will continue to be displayed so long as the switch 102 is activated (222).

If the new zero value is not less than 1 sccm (216), the message "Zero Error!! See Manual" is displayed upon display 13. This message will be displayed so long as the switch 102 is activated (228). When the switch 102 is no longer activated, the new zero value is discarded and the old zero value used in its place (230).

With respect to the above description, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. A valve assembly comprising:

an inlet valve;

an outlet valve;

a bypass line in fluid communication with the inlet valve and the outlet valve;

a flow sensor line in fluid communication with the inlet valve and the outlet valve, the flow sensor line further comprising a flow sensor; and a means for alternately directing fluid flow the bypass line and the flow sensor line in such manner that flow through the valve assembly is constant.

2. The valve assembly of claim 1 wherein the inlet valve further comprises an inlet valve body and the outlet valve further comprises an outlet valve body, the bypass line being in fluid communication with the inlet valve body through an inlet bypass passageway and with the outlet valve body through an outlet bypass passageway, and the flow sensor line being in fluid communication with the inlet valve body through an inlet sensor flow passageway and with the outlet valve body through an outlet sensor flow passageway.

3. The valve assembly of claim 2 wherein the inlet bypass passageway is formed opposite the inlet flow sensor passageway and the outlet bypass passageway is formed opposite the outlet flow sensor passageway.

4. The valve assembly of claim 3 further comprising a valve rotor having an inlet end and an outlet end, the inlet end being received in the inlet valve body and the outlet end being received in the outlet valve body, the inlet end having an inlet passageway alternatively communicable with the inlet bypass passageway and the inlet flow sensor passageway, and the outlet end having an outlet passageway alternatively communicable with the outlet bypass passageway and the outlet flow sensor passageway.

5. The valve assembly of claim 4 wherein the inlet passageway further comprises a longitudinal portion and a transverse portion, the inlet passageway transverse portion being aligned with the inlet bypass passageway and the inlet flow sensor passageway, and wherein the outlet passageway further comprises a longitudinal portion and a transverse portion, the outlet passageway transverse portion being aligned with the outlet bypass passageway and the outlet flow sensor passageway, the inlet passageway transverse portion and the outlet passageway transverse portion being aligned in such manner that when the inlet passageway transverse portion is aligned with the inlet bypass passageway the outlet passageway transverse portion is aligned with the outlet bypass passageway and when the inlet passageway transverse portion is aligned with the inlet sensor flow passageway the outlet passageway transverse portion is aligned with the outlet sensor flow passageway.

6. The valve assembly of claim 5 wherein the inlet passageway transverse portion further comprises an eccentric groove formed proximate a lateral surface of the valve rotor and wherein the outlet passageway transverse portion further comprises an eccentric groove formed proximate the lateral surface of the valve rotor.

7. The valve assembly of claim 4 further comprising a switch actuator fixedly attached to the valve rotor, the switch actuator operable to activate a switch in a bypass position wherein gas flow is diverted through the bypass line.

8. The valve assembly of claim 7 further comprising a stop, the switch actuator being engageable to the stop in a sensor flow position wherein gas flow is diverted through the sensor flow line.

\* \* \* \* \*